United States Patent [19]

Gocho et al.

[11] Patent Number: 5,763,233
[45] Date of Patent: Jun. 9, 1998

[54] PROCESS FOR THE PRODUCTION OF δ DECALACTONE

[75] Inventors: Shinobu Gocho, Tokyo; Kitazawa Rumi, Zama; Komai Tsuyoshi, Sagamihara, all of Japan

[73] Assignee: T. Hasegawa Co., Ltd., Tokyo, Japan

[21] Appl. No.: 903,919

[22] Filed: Jul. 31, 1997

[30] Foreign Application Priority Data

Aug. 2, 1996 [JP] Japan ................. 8-219051

[51] Int. Cl.$^6$ ................................ C12P 17/06
[52] U.S. Cl. ............ 435/125; 435/124; 435/822; 435/928; 435/832; 435/859; 435/873; 435/875; 435/876; 435/877; 435/910
[58] Field of Search .................. 435/124, 125, 435/822, 828, 832, 859, 873, 875, 876, 877, 910

[56] References Cited

U.S. PATENT DOCUMENTS

| | | | |
|---|---|---|---|
| 5,032,513 | 7/1991 | Page et al. | 435/125 |
| 5,128,261 | 7/1992 | Delaat et al. | 435/125 |
| 5,215,901 | 6/1993 | Boog et al. | 435/125 |
| 5,527,693 | 6/1996 | Cardillo et al. | 435/125 |

FOREIGN PATENT DOCUMENTS

| | | |
|---|---|---|
| 0425001 | 5/1991 | European Pat. Off. . |
| 0577463 | 1/1994 | European Pat. Off. . |
| 3-155792 | 7/1991 | Japan . |
| 6-225781 | 8/1994 | Japan . |

OTHER PUBLICATIONS

Biotech Abs 92–05740 van der Schaft et al Appl. Microbiol. Biotech 36, 6, pp. 712–716 (1992).

van der Schaft et al., "Microbial production of natural δ-decalactone and δ-dodecalactone from the corresponding α,β-unsaturated lactones in Massoi bark oil", Appl Microbiol Biotechnol (1992) 36:712–716.

Gen'ichi Indo, "Synthetic Perfumes", pp. 564–565, Kagaku Kogyo Nippo-sha, 1996.

Primary Examiner—Herbert J. Lilling
Attorney, Agent, or Firm—Wenderoth, Lind & Ponack, L.L.P.

[57] ABSTRACT

This invention provides a process for the production of δ-decalactone by the microbial reduction of massoia lactone, characterized in that a bacterium having the ability to reduce massoia lactone is used as the microorganism. The δ-decalactone produced according to this process has a highly tastable, mild creamlike scent and flavor, and is hence suitable for use in flavor compositions.

8 Claims, No Drawings

PROCESS FOR THE PRODUCTION OF δ DECALACTONE

This invention relates to a process for the production of δ-decalactone with the aid of a microorganism.

More particularly, it relates to a process for the production of δ-decalactone by the microbial reduction of massoia lactone.

δ-Decalactone is known to be a flavor compound having a strong, sweet creamlike or nutlike scent, and has conventionally been used as an ingredient for the preparation of flavor compositions. In order to produce this compound by chemical synthesis, there have been proposed, for example, a process in which 2-cyclopentanone is oxidized with a peroxy acid, and a process in which 2-cyclopentanone is converted into 5-hydroxydecanoic acid and the latter is then lactonized (Gen'ichi Indo, "Synthetic Perfumes", page 565, Kagaku Kogyo Nippo-sha, 1996).

On the other hand, in order to produce δ-decalactone by microbial conversion, there have been proposed, for example, a process for producing 5-decanolide from natural 2-decen-1,5-olide by utilizing the reducing power possessed by a yeast (e.g., Saccharomyces cerevisiae) or a fungus (e.g., Polyporus durus) (Japanese Patent Laid-Open No. 155792/'91; EP-A-425001), and a process for producing δ-decanolide, δ-dodecanolide or a mixture thereof by the biohydrogenation of a substrate containing the corresponding unsaturated lactone (i.e., δ-decen-2-olide, δ-dodecen-2-olide or a mixture thereof) with the aid of a yeast such as Saccharomyces delbrueckii (Japanese Patent Laid-Open No. 225781/'94; EP-A-577463).

In recent years, there is a growing tendency to the use of natural materials for the manufacture of food and cosmetic additives including flavors and perfumes. Consequently, it is strongly desired in the field of flavor industry to develop flavors obtainable without using chemical synthesis techniques, such as natural flavors harvested from natural source materials, and flavors produced by fermentation techniques using microorganisms. In addition, δ-decalactone produced by chemical synthesis techniques lacks a naturally mild creamlike scent or flavor and is not always satisfactory when used as an ingredient for the preparation of flavor compositions. Moreover, a process for harvesting δ-decalactone from natural source materials is also employed. However, the contents of flavor components in natural source materials are generally low, so that this process is not suitable for practical purposes because of high cost requirements.

On the other hand, in order to produce δ-decalactone by microbial conversion, a process utilizing the reducing power of a fungus and, in particular, a yeast has been proposed as described above. However, the conversion of materials by utilizing the reducing power of a yeast has the disadvantages that it is difficult to effect the reaction at high substrate concentrations and it takes a long time to obtain the desired product.

Accordingly, it is the primary object of the present invention to provide a novel process for the production of δ-decalactone by the microbial reduction of massoia lactone in which the reaction can be effected at a high substrate concentration and in a short incubation time.

The present inventors have made intensive investigations with a view to solving the above-described problems, and have now discovered that certain bacteria (in particular, bacteria belonging to the genera Pseudomonas, Proteus, Bacillus, Cellulomonas, Micrococcus, Xanthomonas and Acetobacter, and more specifically, bacteria such as Pseudomonas aeruginosa, Pseudomonas fluorescens, Pseudomonas putida, Bacillus subtilis, Proteus vulgaris, Cellulomonas biazotea, Micrococcus luteus, Xanthomonas maltophilia and Acetobacter xylinum) have a great ability to reduce massoia lactone, and δ-decalactone can be efficiently produced from massoia lactone by using these bacteria. Since it has not been known at all in the prior art that bacteria have the ability to reduce massoia lactone, the fact that the above-described bacteria have a great ability to reduce massoia lactone to δ-decalactone is a very surprising and entirely new discovery.

Thus, the present invention provides a process for the production of δ-decalactone by the microbial reduction of massoia lactone, characterized in that a bacterium having the ability to reduce massoia lactone is used as the microorganism.

The process of the present invention is more specifically described hereinbelow.

The microorganisms which can be used for the production of δ-decalactone by the microbial reduction of massoia lactone according to the present invention include bacteria having the ability to reduce massoia lactone to δ-decalactone and, in particular, bacteria belonging to the genera Pseudomonas, Proteus, Bacillus, Cellulomonas, Micrococcus, Xanthomonas and Acetobacter. Preferred examples of useful bacteria include Pseudomonas aeruginosa, Pseudomonas fluorescens, Pseudomonas putida, Bacillus subtilis, Proteus vulgaris, Cellulomonas biazotea, Micrococcus luteus, Xanthomonas maltophilia and Acetobacter xylinum. More specifically, there may be used bacterial strains deposited with public stock culture institutions as type cultures, such as Pseudomonas aeruginosa IFO 3447, Pseudomonas fluorescens ATCC 13525 (=JCM 5963), Pseudomonas putida ATCC 33015 (=JCM 6156), Bacillus subtilis ATCC 6633 (=IAM 1069), Proteus vulgaris IAM 1025, Cellulomonas biazotea IFO 12680, Micrococcus luteus IFO 12708, Xanthomonas maltophilia JCM 1982 and Acetobacter xylinum IFO 3288. However, the process of the present invention is not limited to the use of these bacteria, and any other bacteria that have the ability to reduce the carbon-to-carbon double bond in massoia lactone may likewise be used.

The official names and addresses of the public stock culture institutions represented by the abbreviations "IFO", "ATCC", "JCM" and "IAM" as used herein are as follows. The above-described bacterial strains may readily be obtained by giving an order to the respective institutions.

IFO: INSTITUTE FOR FERMENTATION OSAKA 17-85, Juso-honmachi 2-chome, Yodogawa-ku, Osaka 532, Japan ATCC: American Type Culture Collection 12301 Parklawn Drive Rockville, Md. 20852, U. S. A.

JCM: Japan Collection of Microorganisms RIKEN Wako, Saitama 351-01, Japan

IAM: IAM Culture Collection Center for Cellular and Molecular Research Institute of Molecular and Cellular Biosciences The University of Tokyo 1-1, Yayoi 1-chome, Bunkyo-ku, Tokyo 113, Japan The massoia lactone used as the starting material in the present invention may be a synthetic product or a natural material. Especially preferred are massoi bark oil and purified products thereof. They may readily be obtained as commercial products.

The process for the production of δ-decalactone by reducing massoia lactone with the aid of a bacterium as described above may be carried out according to any of various procedures. They include, for example, a procedure which comprises adding massoia lactone to a culture medium containing a carbon source, a nitrogen source, inorganic salts and the like, and culturing the bacterium therein; a procedure which comprises precuituring the bacterium in a culture medium containing a carbon source, a nitrogen source, inorganic salts and the like for about 1 to 3 days, adding massoia lactone to the culture medium, and further culturing the bacterium therein; a procedure which comprises culturing the bacterium in a culture medium containing a carbon source, a nitrogen source, inorganic salts and the like, collecting bacterial cells by centrifugation or other means, dispersing the bacterial cells in a buffer solution or the like, adding massoia lactone thereto, and effecting the reaction thereof; and a procedure which comprises immobilizing the bacterium according to a per se known technique, placing it in a suitable medium containing massoia lactone, and effecting the reaction thereof.

The carbon sources which can be incorporated in the culture medium include, for example, sugars such as glucose and fructose; organic acids such as citric acid and malic acid; and alcohols such as ethanol and glycerol. Usable nitrogen sources include, for example, inorganic nitrogen compounds such as ammonium sulfate and ammonium nitrate; and organic nitrogen sources such as peptone. Usable inorganic salts include, for example, various phosphates and magnesium sulfate. Moreover, slight amounts of metals (e.g., iron salts and calcium salts) may be incorporated in the culture medium as required.

If the process for the production of 5-decalactone from massoia lactone in accordance with the resent invention is carried out in the presence of an organic solvent capable of dissolving massoia lactone and hardly soluble in water, δ-decalactone can be produced efficiently. Usable organic solvents include, for example, vegetable fats and oils such as soybean oil, olive oil, rice bran oil, peanut oil, sesame oil, safflower oil, linseed oil, walnut oil, sunflower oil, rapeseed oil and camellia oil; animal fats and oils such as sardine oil, herring oil, mackerel oil, cod liver oil and cuttlefish liver oil; fatty acid monoglycerides, fatty acid diglycerides, fatty acid triglycerides, fatty acids and phospholipids; and aliphatic and aromatic hydrocarbons such as liquid paraffin, hexane and toluene. Among others, soybean oil, olive oil and liquid paraffin are preferred.

The concentration of massoia lactone added to the culture medium cannot be specifically defined, because it may vary according to the culture method and the like. However, it is generally in the range of 5 to 50 g/L and preferably 10 to 30 g/L.

Moreover, the amount in which the organic solvent capable of dissolving massoia lactone and hardly soluble in water is added to the culture medium cannot be specifically defined, because it may vary according to the type of the organic solvent, the cultivation conditions and the like. However, it is generally in the range of about 50 to about 1,000 parts by weight, and preferably about 200 to about 800 parts by weight, per 100 parts by weight of massoia lactone.

As the culture method, there may be employed any of various methods such as shaking culture and aerobic agitation culture. The incubation temperature is usually in the range of about 15° to 40° C. and preferably about 20° to 35° C., and the pH is preferably in the range of about 6 to about 8. Although the cultivation period is not critical, it may range, for example, from 1 to 5 days.

One preferred embodiment of the process for the production of δ-decalactone from massoia lactone in accordance with the present invention is as follows. A culture medium is prepared by adding about 1 to about 3 parts by weight of massoia lactone and about 1 to about 10 parts by weight of an organic solvent capable of dissolving massoia lactone and hardly soluble in water (e.g., soybean oil or olive oil) to 100 parts by weight of an inorganic salt medium (consisting essentially of an inorganic nitrogen source) or natural medium (e.g., bouillon medium) having a pH of about 6 to about 7.5. Then, a bacterial strain as described above is cultured in this culture medium under shaken or agitated conditions at a temperature of about 20° to about 35° C. and preferably about 25° to about 33° C. for a period of about 40 to about 60 hours. Thus, δ-decalactone can be obtained in high yield.

If desired, using a suitable separating means such as decantation, centrifugation or solvent extraction, the δ-decalactone-containing fermentation fluid obtained as a result of the above-described cultivation may be treated to separate a δ-decalactone-containing oily layer therefrom. Moreover, if necessary, this oily layer may be dehydrated by adding thereto any suitable dehydrating agent such as anhydrous sodium sulfate, silica gel or powdered filter paper, and may further be purified by a means such as distillation or column chromatography. Thus, high-purity and high-quality δ-decalactone may readily be obtained.

The δ-decalactone produced according to the process of the present invention using a bacterium has a persistent mild creamlike scent and flavor, and can hence be used as an ingredient for the preparation of various types of highly tastable and mild flavor compositions.

The present invention is further illustrated by the following examples.

EXAMPLE 1

A 500-ml shouldered flask was charged with 100 ml of M medium (whose composition and pH are given below) and 6 g of soybean oil, and sterilized at 120° C. for 20 minutes. After cooling, 2 g of sterilized massoi bark oil (containing 55% of massoia lactone) was added thereto. Then, the resulting culture medium was inoculated with *Bacillus subtilis* ATCC 6633 which had been precultured in advance, and incubated at 30° C. for 48 hours in a reciprocal shaker having a shaking speed of 120 times per minute.

After completion of the incubation, the culture medium was analyzed by gas chromatography. This revealed that the degree of conversion of massoia lactone in the added massoi bark oil to δ-decalactone was 40%.

| (M medium) | |
|---|---|
| Peptone (manufactured by Kyokuto Pharmaceutical Co., Ltd.) | 1% |
| Meat extract (manufactured by Kyokuto Pharmaceutical Co., Ltd.) | 0.5% |
| Sodium chloride | 0.5% |
| pH | 6.85 |

COMPARATIVE EXAMPLE 1

The procedure of Example 1 was repeated, except that 5% of raw yeast (manufactured by Oriental Yeast Co., Ltd.) was added in place of *Bacillus subtilis* ATCC 6633. As a result, the degree of conversion to δ-decalactone was 3%.

EXAMPLE 2

A 500-ml shouldered flask was charged with 100 ml of M medium having the composition shown in Example 1, and sterilized at 120° C. for 20 minutes. After cooling, 2 g of sterilized massoi bark oil (containing 55% of massoia lactone) was added thereto. Then, the resulting culture medium was inoculated with Pseudomonas putida ATCC 33015 which had been precultured in advance, and incubated at 30° C. for 48 hours in a reciprocal shaker having a shaking speed of 120 times per minute.

After completion of the incubation, the culture medium was analyzed by gas chromatography. This revealed that the degree of conversion of massoia lactone in the added massoi bark oil to δ-decalactone was 85%.

EXAMPLE 3

A 50-liter fermenter was charged with 30 liters of M medium having the composition shown in Example 1 and 1,800 g of soybean oil, and sterilized at 120° C. for 20 minutes. After cooling, 600 g of sterilized massoi bark oil (containing 55% of massoia lactone) was added thereto. Then, the resulting culture medium was inoculated with Pseudomonas putida ATCC 33015 which had been precultured in advance, and incubated under aerated and stirred conditions for 48 hours at an aeration rate of 5 liters per minute, a stirring speed of 150 rpm and a temperature of 30° C.

After completion of the incubation, the culture medium was analyzed by gas chromatography. This revealed that the degree of conversion of massoia lactone in the added massoi bark oil to δ-decalactone was 99.1%.

The resulting culture was centrifuged to obtain 2,350 g of an oily layer. This oily layer was distilled to obtain 194.8 g of δ-decalactone having a purity of 97%.

EXAMPLE 4~17

Using the following bacterial strains, cultivation and analysis were carried out in the same manner as in Examples 1 and 2. The resulting degrees of conversion to δ-decalactone were as shown in Table 1.

TABLE 1

| Example No. | Bacterial strain | Culture method | Degree of conversion |
|---|---|---|---|
| Example 4 | Pseudomonas aeruginosa IFO 3447 | Example 1 | 33.7% |
| Example 5 | Pseudomonas aeruginosa IFO 3447 | Example 2 | 5.5% |
| Example 6 | Pseudomonas fluorescens ATCC 13525 | Example 1 | 87.3% |
| Example 7 | Pseudomonas fluorescens ATCC 13525 | Example 2 | 7.5% |
| Example 8 | Proteus vulgaris IAM 1025 | Example 1 | 15.3% |
| Example 9 | Proteus vulgaris IAM 1025 | Example 2 | 5.0% |
| Example 10 | Cellulomonas biazotea IFO 12680 | Example 1 | 31.4% |
| Example 11 | Cellulomonas biazotea IFO 12680 | Example 2 | 6.0% |
| Example 12 | Micrococcus luteus IFO 12708 | Example 1 | 18.5% |
| Example 13 | Micrococcus luteus IFO 12708 | Example 2 | 5.0% |
| Example 14 | Xanthomonas maltophilia JCM 1982 | Example 1 | 12.3% |

TABLE 1-continued

| Example No. | Bacterial strain | Culture method | Degree of conversion |
|---|---|---|---|
| Example 15 | Xanthomonas maltophilia JCM 1982 | Example 2 | 5.3% |
| Example 16 | Acetobacter xylinum IFO 3288 | Example 1 | 21.4% |
| Example 17 | Acetobacter xylinum IFO 3288 | Example 2 | 5.2% |

It is evident from the foregoing examples that, in the production of δ-decalactone by the microbial reduction of massoia lactone, the reaction can be effected at a high substrate concentration and in a short period of time, by using specific species of bacteria in place of yeasts which have been used in the prior art.

The δ-decalactone obtained according to the process of the present invention has a highly tastable and mild cream-like scent and flavor, and is hence suitable for use as an ingredient for the preparation of various flavor compositions.

We claim:

1. A process for the production of δ-decalactone by the microbial reduction of massoia lactone, characterized in that a bacterium having the ability to reduce massoia lactone is used as the microorganism.

2. A process as claimed in claim 1 wherein the bacterium is a bacterium belonging to the genus Pseudomonas, Proteus, Bacillus, Cellulomonas, Micrococcus, Xanthomonas or Acetobacter.

3. A process as claimed in claim 1 wherein the bacterium is selected from the group consisting of Pseudomonas aeruginosa, Pseudomonas fluorescens, Pseudomonas putida, Bacillus subtilis, Proteus vulgaris, Cellulomonas biazotea, Micrococcus luteus, Xanthomonas maltophilia and Acetobacter xylinum.

4. A process as claimed in claim 1 wherein the microbial reduction of massoia lactone is carried out in the presence of an organic solvent capable of dissolving massoia lactone and hardly soluble in water.

5. A process as claimed in claim 4 wherein the organic solvent is selected from the group consisting of vegetable fats and oils, animal fats and oils, fatty acid mono-, di- and triglycerides, fatty acids, phospholipids, and aliphatic and aromatic hydrocarbons.

6. A process as claimed in claim 4 wherein the organic solvent is soybean oil, olive oil or liquid paraffin.

7. A process as claimed in claim 4 wherein the organic solvent is used in an amount of 50 to 1,000 parts by weight per 100 parts by weight of massoia lactone.

8. A process as claimed in claim 1 wherein the bacterium having the ability to reduce massoia lactone is cultured in a culture medium containing massoia lactone at a concentration of 5 to 50 g/L.

* * * * *